United States Patent
Greene, Jr. et al.

(10) Patent No.: US 11,389,168 B2
(45) Date of Patent: Jul. 19, 2022

(54) TEMPORARY AORTIC OCCLUSION DEVICE

(71) Applicants: MicroVention, Inc., Tustin, CA (US); University of Virginia Patent Foundation, Charlottesville, VA (US); United States of America as Represented by the Secretary of the Navy, Silver Spring, MD (US)

(72) Inventors: George R. Greene, Jr., Costa Mesa, CA (US); Ivan Sepetka, Los Altos, CA (US); Cathy Lei, Chino Hills, CA (US); Rupal Nguyen, Costa Mesa, CA (US); Matthew J. Bradley, Silver Spring, MD (US); Stephen T. Ahlers, Silver Spring, MD (US); Carl S. Goforth, Silver Spring, MD (US); James R. Stone, Charlottesville, VA (US)

(73) Assignees: MicroVention, Inc., Aliso Viejo, CA (US); University of Virginia Patent Foundation, Charlottesville, VA (US); United States of America as Represented by the Secretary of the Navy, Silver Spring, MD (US)

( * ) Notice: Subject to any disclaimer, the term of this patent is extended or adjusted under 35 U.S.C. 154(b) by 340 days.

(21) Appl. No.: 15/690,152

(22) Filed: Aug. 29, 2017

(65) Prior Publication Data
US 2018/0055515 A1 Mar. 1, 2018

Related U.S. Application Data

(60) Provisional application No. 62/382,705, filed on Sep. 1, 2016.

(51) Int. Cl.
*A61B 17/12* (2006.01)
*A61B 17/00* (2006.01)
*A61B 90/00* (2016.01)

(52) U.S. Cl.
CPC .... *A61B 17/12109* (2013.01); *A61B 17/1204* (2013.01); *A61B 17/12136* (2013.01);
(Continued)

(58) Field of Classification Search
CPC .......... A61B 17/1204; A61B 17/12109; A61B 17/12136; A61B 17/12168;
(Continued)

(56) References Cited

U.S. PATENT DOCUMENTS 5,935,139 A * 8/1999 Bates ................... A61B 17/221
600/1
6,589,264 B1 7/2003 Barbut et al.
(Continued)

FOREIGN PATENT DOCUMENTS

EP 3010563 A2 4/2016
JP 2004-533290 A 11/2004
(Continued)

OTHER PUBLICATIONS

WIPO, International Preliminary Examining Authority (U.S. Patent and Trademark Office), International Preliminary Report on Patentability dated Nov. 3, 2017 in International Patent Application No. PCT/US2017/049202, 7 pages.
(Continued)

*Primary Examiner* — Mohamed G Gabr
(74) *Attorney, Agent, or Firm* — Holland & Hart LLP (57) ABSTRACT

A temporary aortic occlusion device is disclosed, having an expandable locator portion and an expandable occlusion portion. The expandable locator portion assists a user in determining whether the distal end of the device has been
(Continued)

advanced within a patient's aorta, and the occlusion portion is expanded to occlude the patient's aorta, preferably below the renal arteries.

19 Claims, 8 Drawing Sheets

(52) U.S. Cl.
CPC .. *A61B 17/12168* (2013.01); *A61B 17/12172* (2013.01); *A61B 17/12177* (2013.01); *A61B 2017/00115* (2013.01); *A61B 2017/1205* (2013.01); *A61B 2090/0807* (2016.02)

(58) Field of Classification Search
CPC ........ A61B 17/12172; A61B 17/12177; A61B 2017/00115; A61B 2017/1205; A61B 2090/0807
See application file for complete search history.

(56) References Cited

U.S. PATENT DOCUMENTS

| | | |
|---|---|---|
| 7,278,430 B2 | 10/2007 | Kumar |
| 9,474,882 B2 | 10/2016 | Franklin |
| 2002/0161394 A1 | 10/2002 | Macoviak et al. |
| 2003/0135257 A1 | 7/2003 | Taheri |
| 2004/0006370 A1 | 1/2004 | Tsugita |
| 2004/0064092 A1 | 4/2004 | Tsugita et al. |
| 2006/0058833 A1 | 3/2006 | VanCamp et al. |
| 2007/0167980 A1 | 7/2007 | Figulla et al. |
| 2007/0265656 A1 | 11/2007 | Amplatz et al. |
| 2010/0114017 A1 | 5/2010 | Lenker et al. |
| 2011/0172697 A1 | 7/2011 | Jönsson |
| 2012/0109057 A1* | 5/2012 | Krolik .............. A61B 17/32053 604/103.01 |
| 2013/0096499 A1* | 4/2013 | Tchirikov ........... A61B 17/0057 604/101.05 |
| 2014/0121674 A1* | 5/2014 | Staunton .............. A61N 1/0558 606/129 |
| 2014/0214067 A1* | 7/2014 | Sachar .................... A61F 2/013 606/194 |
| 2014/0257361 A1* | 9/2014 | Prom ............... A61B 17/12022 606/198 |
| 2014/0336690 A1 | 11/2014 | Zhadkevich |
| 2015/0005808 A1 | 1/2015 | Chouinard et al. |
| 2016/0015397 A1 | 1/2016 | Figulla et al. |

FOREIGN PATENT DOCUMENTS

| | | |
|---|---|---|
| JP | 2015-110113 A | 6/2015 |
| WO | WO 96/40347 A1 | 12/1996 |
| WO | 02/085443 A1 | 10/2002 |
| WO | 2010/121049 A9 | 10/2010 |
| WO | WO 2014/134215 A1 | 9/2014 |

OTHER PUBLICATIONS

Extended European Search Report dated Apr. 8, 2020, issued in European Patent Application No. 17847403.7.

\* cited by examiner

TEMPORARY AORTIC OCCLUSION DEVICE

RELATED APPLICATIONS

This application claims priority to U.S. Provisional Application Ser. No. 62/382,705 filed Sep. 1, 2016 entitled Temporary Aortic Occlusion Device, which is hereby incorporated herein by reference in its entirety.

BACKGROUND OF THE INVENTION

This application relates to a temporary aortic occlusion device for controlling torso hemorrhage.

Traumatic hemorrhage, primarily the result of blast injuries, is the leading cause of death in active-duty military service members. Although the widespread use of tourniquets has helped to reduce loss of life from severe lower extremity injury, non-compressible torso hemorrhage remains a challenge with high mortality given the relative anatomic inaccessibility of this region to obtain hemorrhage control.

Reports have suggested that up to 25% of hemorrhage sustained in the battlefield is potentially survivable with 50% the result of truncal trauma. Pelvic bleeding, in particular, can be severe and difficult to control, requiring advanced, upper echelon hospital-based care, such as angioembolization, for definitive treatment. Because these advanced care methods and specially trained operators are at higher levels of care, mortality remains high. Unfortunately, outside of pelvic binders for pelvic fracture stabilization, which have limited success in hemorrhage control and are of no value in penetrating trauma there, has been little advancement in the control of non-compressible torso bleeding at the lower echelons of care.

Traditionally, early temporary control for non-compressible torso hemorrhage has been limited to thoracotomy with aortic cross-clamping. This technique has been reserved for moribund patients with absent or lost pulses and has an associated high morbidity and mortality. With growing interest in endovascular techniques for the management of vascular trauma the use of a resuscitative endovascular balloon occlusion of the aorta (REBOA) as an alternative to thoracotomy has been reported. For patients with massive pelvic or intra-abdominal hemorrhage who survive transport to an advanced care facility, placement of a temporary occlusion balloon in the infra-renal aorta, proximal to the aortic bifurcation, or the within the descending thoracic aorta have been used to provide time for more definitive treatment through surgical or endovascular methods. This in-hospital technique provides a method to stop flow of blood below the level of the balloon until the balloon can be deflated under controlled conditions. Insertion of an occlusive balloon is less invasive than a thoracotomy and can be placed in the unstable patient. Endovascular balloon occlusion has been shown to be lifesaving and superior to thoracotomy with aortic cross-clamping in civilian literature.

Placement of a temporary occlusion balloon in the aorta is performed under sterile conditions using ultrasound and fluoroscopic guidance, which requires time, skill, and bulky portable x-ray machines. Despite the potentially life-saving nature of aortic balloon occlusion in the setting of massive torso and/or pelvic hemorrhage, current approaches for the placement these devices require fluoroscopic guidance. Fluoroscopy allows for: (i) intra-arterial injection of contrast dye to define the vascular anatomy, (ii) positioning of an aortic occlusion balloon with respect to this defined anatomy, and (iii) precise control of inflation of the device to allow for sufficient occlusion of the aorta while avoiding over-inflation that could result in rupture of the aorta secondary to balloon inflation.

A technique has been performed utilizing inflation of an aortic occlusion balloon in a trauma bay as a temporary measure for patients with massive pelvic hemorrhage and life-threatening shock, without fluoroscopic guidance. However, this approach requires the expertise of a senior Interventional Radiologist to interpret subtle tactile cues reflecting appropriate balloon placement and inflation. Further, this technique was performed in a "blind" fashion and relied upon the assumption of normal vascular anatomy. In spite of the reported success with balloon occlusion placement, positioning and confirmation has required valuable time, the use of fluoroscopic imaging, and skilled experienced practitioners at higher echelons of care. Additionally, due to the size of the currently available device surgery is required to repair the arteriotomy created by the catheter.

Any non-fluoroscopic approach for temporary occlusion of the aorta in the setting of hemorrhage should address: (i) positioning of the device with respect to individual patient anatomy, (ii) controlled inflation of the balloon or other occlusion device to account for varying aorta diameters, particularly in the under-resuscitated patient, (iii) a low profile, allowing for removal of the device without surgical repair, and (iv) must account for considerations related to the need for operator training in how to safely introduce the device into the femoral artery without creation of additional vascular injury.

Placement of a temporary aortic occlusion device may become an effective technique for hemorrhage control at lower echelons of care if it could be adapted for quicker, easier insertion by non-endovascular specialized providers. For example, Role II facilities such as the Navy Afloat Trauma System (NATS), the Navy/Marine Corps Forward Resuscitative Surgical Systems (FRSS), or Role I settings with Independent Duty Corpsmen and Navy Special Warfare SEAL corpsmen and physicians. Earlier availability of this technique could allow first-responders to stabilize non-compressible torso bleeding until advanced care was available resulting in decreased mortality.

The present invention addresses the need to improve forward surgical applications and targeted therapy for hemorrhagic injury.

SUMMARY OF THE INVENTION

The present invention is directed to a temporary aortic occlusion device having an expandable locator portion and an expandable occlusion portion. The expandable locator portion assists a user in determining whether the distal end of the device has been advanced within a patient's aorta, and the occlusion portion is expanded to occlude the patient's aorta, preferably below the renal arteries.

In one embodiment, the locator portion has a maximum expansion diameter that is smaller than a maximum expansion diameter of the occlusion portion. Additionally, the locator portion preferably has a maximum expansion diameter that is the same size or slightly smaller than the internal diameter of a patient's aorta, providing the user with little or no resistance to expansion when positioned in an aorta.

In one embodiment, the locator portion and the occlusion portion are each composed of a plurality of braided mesh wires. Both portions can be coated, laminated, or otherwise covered with a polymer.

In another embodiment, the occlusion portion can include multiple layers of braided wires. These layers can be created from discrete tubular mesh structures or a single, inverted, tubular mesh structure. In another embodiment, the occlusion portion can include an expandable disc structure, woven fabric, and/or spring-biased struts.

In one embodiment, the locator portion is located distal of the occlusion portion. In another embodiment, the locator portion is located proximal of the occlusion portion.

In another embodiment, the occlusion portion is a balloon that can be inflated with a fluid from a proximal end of the device.

The present invention is also directed to a method of temporarily occluding the aorta of a patient by inserting a temporary aortic occlusion device into a femoral sheath and towards the common iliac bifurcation. An actuation mechanism on the handle of the device is actuated to increase a diameter of a locator on a distal end of the device. If resistance is encountered with the locator, the device is advanced further until the locator can be increased in diameter without resistance. Next, an occluder on the distal end of the device is increased in diameter to occlude the patient's aorta.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIGS. 1-5 are directed to a temporary aortic occlusion device 100 that has a radially expandable mesh locator 104 and a radially expandable mesh occlusion portion 102. The device 100 can be loaded in a femoral sheath (e.g., 6F Sheath) and advanced into the common iliac towards the aortic bifurcation target. Once the distal end of the device 100 is close to the target, the mesh locator 104 can be expanded and, if no resistance to the locator 104 occurs, the mesh occlusion portion 102 can be expanded to occlude the aorta.

The locator 104 is preferably composed of a wire mesh (e.g., 0.0005"-0.004" Nitinol wires) braided into a generally tubular shape. A proximal end of the locator 104 is fixed to distal end of a kink-resistant catheter tube 106 and a distal end of the locator 104 is fixed to ring 114, which is also connected to control wire 109. The control wire 109 is positioned within the lumen of the catheter tube 106 and its proximal end is fixed to slider 112. Hence, as the slider 112 is moved proximally, the control wire 109 moves the ring 114 proximally towards the catheter tube 106, causing the locator 104 to expand. The fully expanded locator 104 can be one of many different sizes, each of which designed to have a maximum expansion that is equal to or smaller than the target aorta size (e.g., 18 mm to 25 mm). The mesh of the locator 104 also may include an elastic hydrophilic coating to prevent blood flow from entering the catheter tube 106.

The occlusion portion 102 functions in a similar manner as the locator 104, having a proximal end fixed to ring 114 and a distal end fixed to ring 116. The ring 116 is further connected to control wire 107, which is slidably positioned within the lumen of the catheter tube 106 and has a proximal end connected to slider 110. Hence, as the slider 110 is moved proximally, it causes the occlusion portion 102 to expand.

The occlusion portion 102 is composed of a wire mesh (e.g., (e.g., 0.0005"-0.004" Nitinol or PET wires) that are laminated, coated (e.g., dip coating), or have a film applied either on its inner surface, outer surface, or both. Coating materials include polyurethane or silicone, and film materials includes polyethylene, linear low-density polyethylene, polyethylene terephthalate, and Nitinol. In one specific example, each of the wires are first coated in a polymer coating (e.g., polyurethane or polyethylene), braided, and then the inner surface of the occlusion portion 102 is completely coated in a thin 10-15 micron film of the same or similar polymer coating. In another specific example, ePTFE is coated on the inner and outer surface of the occlusion portion 102, "sandwiching" its braid. The occlusion portion 102 optionally has a length greater than that of the locator 104, so as to create a sufficient seal with the patient's aorta.

Preferably, the locator 104 and the occlusion portion 102 are spaced to ensure that the occlusion portion 102 does not occlude the renal arteries leading to the kidneys. A preferred average spacing between the two is about 4.00 cm to about 4.50 cm from each other based on the aortic anatomy of a range of average humans. However, it may be desirable to increase this distance in some circumstances (e.g., large patients) or decrease this distance (e.g., young/small patients).

One aspect of the device 100 is that it allows a user to sense whether there is resistance to expanding the locator 104 or not. In this respect, the locator 104 preferably has a maximum diameter expansion that is either the same size as or slightly smaller than the patient's aorta diameter (e.g., 18 mm to 25 mm). This expansion limit can be limited by the length of movement of the slider 112, as well as the construction of the braid. In contrast, the occlusion portion 102 is configured to have a slightly larger maximum expansion diameter than the locator 104 and/or patient's aorta. This allows the occlusion portion 102 to properly engage the aorta and occlude blood flow. If the device 100 only included the occlusion portion 102 and not the locator 104, a user would encounter expansion resistance prior to entering the aorta, as well as in the aorta, which could cause user-confusion about the device's position. By including the locator 104 that will not substantially encounter resistance in the aorta, the user can have a much higher degree of confidence that the device has entered the aorta.

Since the occlusion portion 102 must be capable of expanding within an aorta 1 and applying a reasonably sufficient force again walls of the aorta 1, there is a risk of rupturing or dissecting the smaller vessels connected to the aorta 1 if expanded too soon. In that regard, the locator 104 can be configured to assist expansion only until encountering a predetermined resistance force and/or with a less forceful expansion force. In this regard, the locator 104 can be expanded with less risk of rupturing the smaller, aortic-adjacent vessels.

One way to achieve this reduced expansion force is to compose the locator 104 of relatively fewer braided wires that, when encountering small amounts of force tend to deform or at least provide less force on the vessels (e.g., 36 0.005" wires for the locator 104 vs. 48 0.005" wires for the occlusion portion 102). Additionally, as previously mentioned, the locator 104 can be coated or laminated with a polymer material similar to the occlusion portion 102, which can further create resistance to expansion. Providing a relatively thick coating can further disperse force from the wires of the locator 104, thereby further reducing risk of vessel rupture.

An alternate or additional mechanism includes adding a spring or elastic member between the end of the control wire 109 and the ring 114, such that when resistance is encountered by the locator 104, the spring or elastic expands. Alternately or additionally, the entire control wire 109 can be composed of an elastic material that tends to stretch when resistance is encountered by the locator 104. Optionally, similar mechanisms can be included with regard to the occlusion portion 102, though with the ability to apply somewhat greater force before attenuation.

The handle 108 of the device 100 may also include an indicator light 120 that illuminates when the locator 104 has fully expanded. The handle 108 may have a contact or switch that is triggered when the slider 112 is slid to its proximal-most position to thereby indicate that the aorta 1 has been reached by the device 100.

The distal end of the device 100 also includes an atraumatic tip 118 that is fixed to ring 116. In one example, the tip 118 is composed of a helically-wound wire or coil and is sufficiently flexible to avoid injuring the aorta 1 of a patient.

In operation, the device is loaded directly into a femoral sheath and pushed distally from the femoral artery and into the common iliac towards the common iliac artery bifurcation. Once the catheter tip is close to the target, the slider 112 can be used to slow expand the locator 104. If resistance occurs, the slider 112 can be pushed distally to collapse the locator 104 and the device can be further advanced distally. Once the slider 112 can open fully without resistance, the slider 112 activates the light 120. Finally, the slider 110 can be moved proximally to expand the occlusion portion 102, blocking or occluding the aorta.

Figure 1:
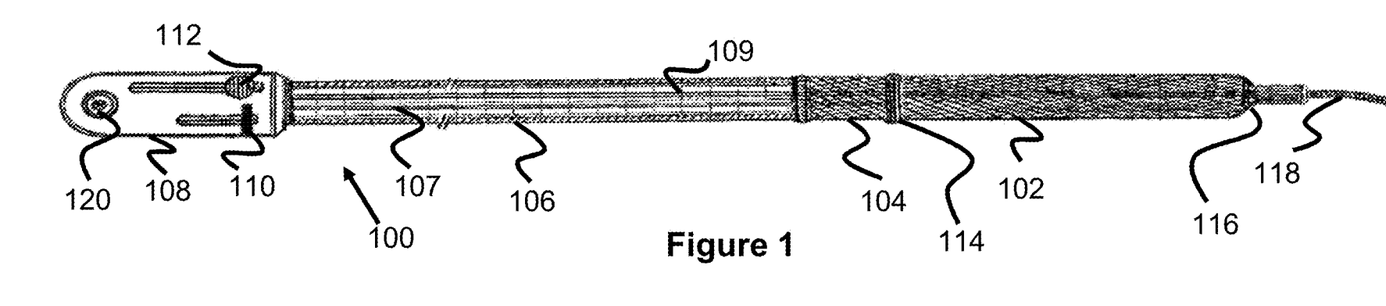
FIG. 1 is a temporary aortic occlusion device according to one embodiment of the present invention utilizing a proximal locator portion and a distal occlusion portion.
Figure 2:
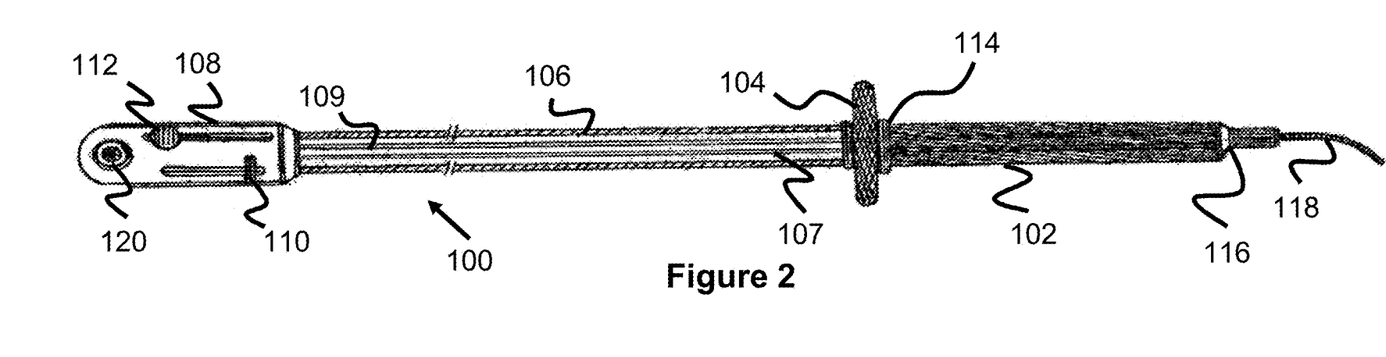
FIG. 2 is the temporary aortic occlusion device according to FIG. 1 where the proximal locator portion is in a radially expanded configuration.
Figure 3:
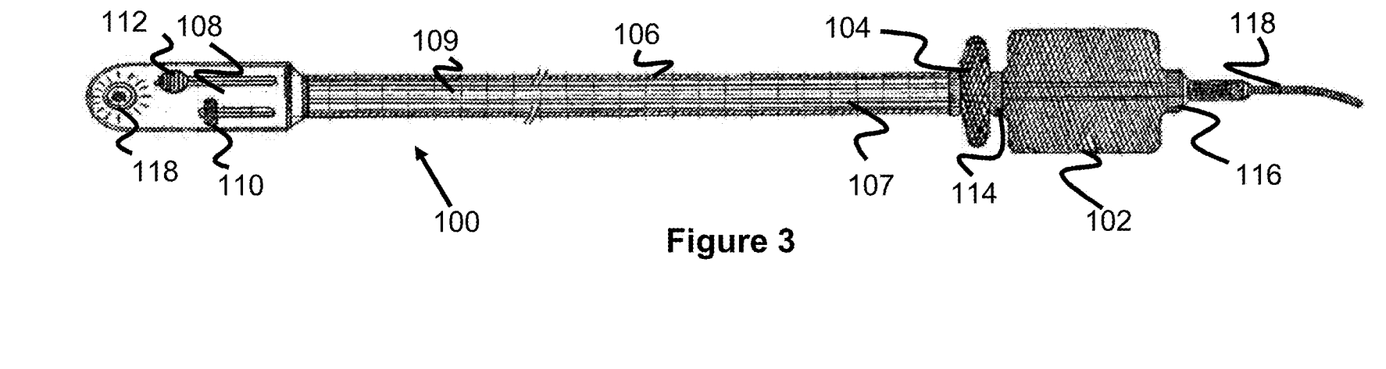
FIG. 3 is the temporary aortic occlusion device according to FIG. 1 where both the proximal locator portion and the distal occlusion portion are in radially expanded configurations.
Figure 4:
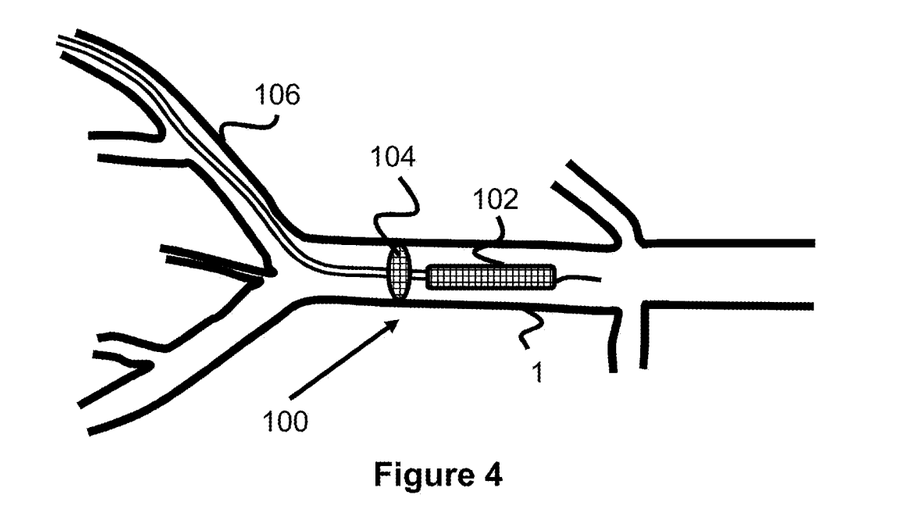
FIG. 4 is the temporary aortic occlusion device according to FIG. 2 in a blood vessel.
Figure 5:
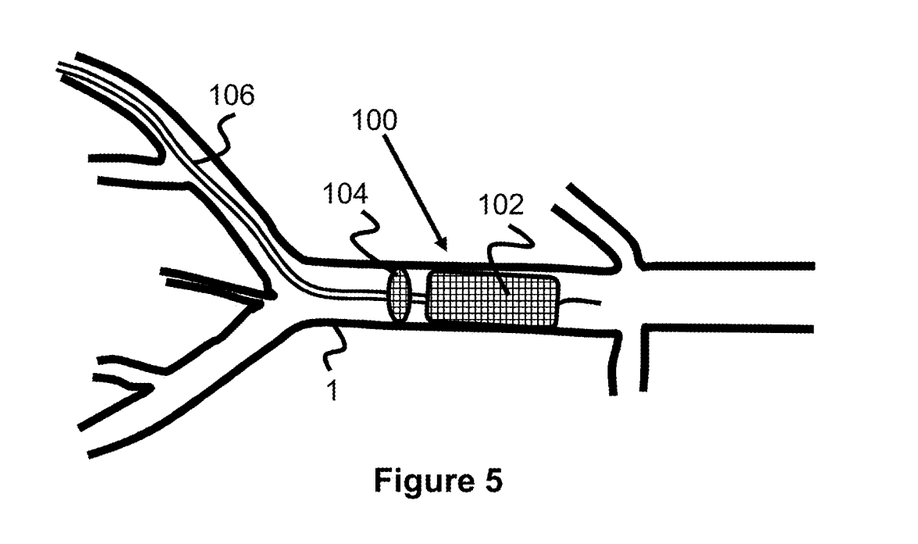
FIG. 5 is the temporary aortic occlusion device according to FIG. 3 in a blood vessel.
Figure 6:
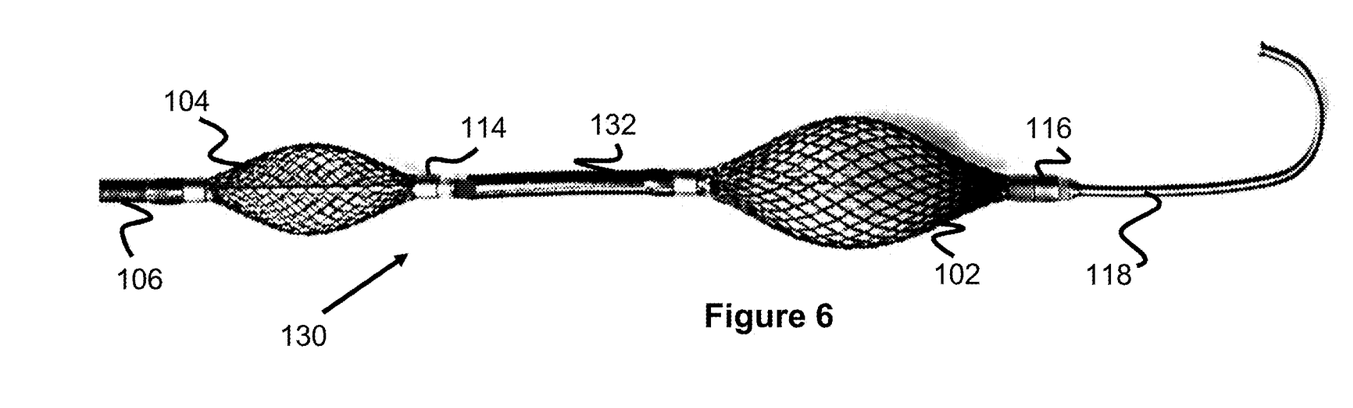
FIG. 6 is a temporary aortic occlusion device according to another embodiment of the present invention.

FIG. 6 illustrates another embodiment of an occlusion device 130 that is generally similar to the previously described device 100, however, the locator 104 is spaced apart from the occlusion portion 102 by tubular element 132. This embodiment may be useful if occlusion is desired at a higher location in the patient's aorta.

Figure 7:
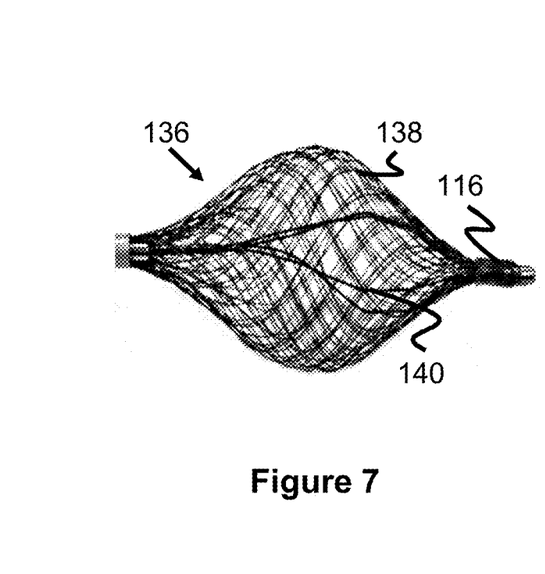
FIG. 7 is a temporary aortic occlusion device occlusion portion according to one embodiment of the present invention.

FIGS. 7-13 illustrate various alternate embodiments of the occlusion portion. For example, FIG. 7 illustrates an occlusion portion 136 braided from a plurality of wires 138 and having a plurality of wire struts 140 disposed within its cavity and connected to the control wire 107. The struts 140 are configured to provide a slight bias or spring-force to help urge the occlusion portion 136 to its expanded configuration. Specifically, the struts 140 can be metal wires connecting between the proximal and distal end of the occlusion portion 136 and that have a shape-memory configuration of a curve (e.g., a curve shape heat set into a shape memory alloy). In a compressed configuration, the struts 140 are relatively straight, but the shape-memory curve of the struts 140 provides an amount of force on the distal end of the occlusion portion 136 to assist the user in its expansion. Alternately, the struts 140 can be configured to return to a relatively straight configuration, biasing the occlusion portion 136 to its compressed configuration. While not shown, the occlusion portion 136 can be laminated, sealed, or otherwise coated in flexible layer of material, as described for other embodiments in this specification.

Figure 8:
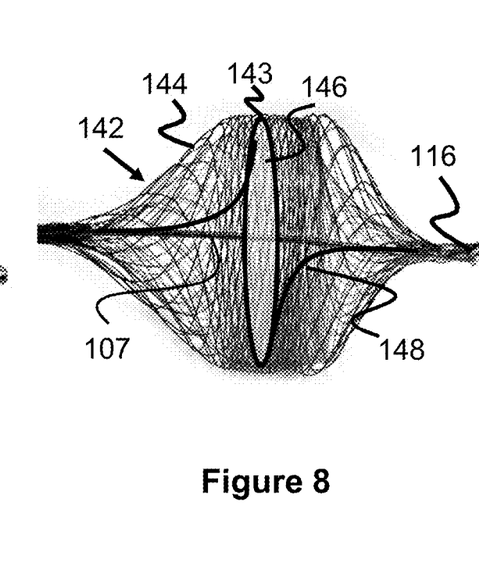
FIG. 8 is a temporary aortic occlusion device occlusion portion according to another embodiment of the present invention.

FIG. 8 illustrates another embodiment of an occlusion portion 142 that is composed of a plurality of braided wires 144. Within the braided wires 144 is a framework comprised of at least a proximal and distal support wires 148 connected to a circular support wire 143. The support wires 148 are connected to each end of the occlusion portion 142 so that, when expanded, the circular support wire 143 is positioned annularly around an axis of the occlusion portion 142. A polymer film 146 is connected to the circular support wire 143, generally forming a plane perpendicular to the axis of the occlusion portion 142. Since the circular support wire 143 and polymer film 146 is sized to expand to substantially the inner diameter of the inner cavity of the occlusion portion 142, an occlusive barrier is created. The braided wires 144 can be left bare or can include a coating, film, lamination, or other occlusive materials as described elsewhere in this specification.

Figure 9:
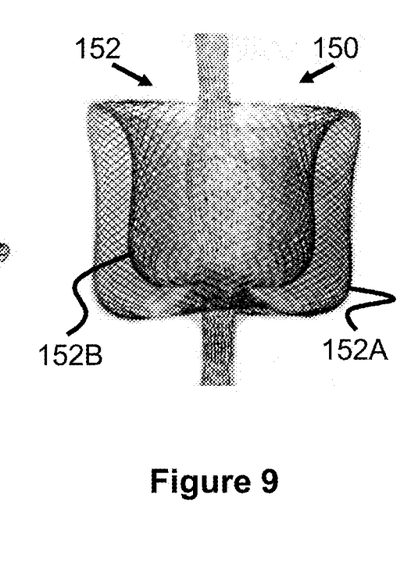
FIG. 9 is a temporary aortic occlusion device occlusion portion according to another embodiment of the present invention.

FIG. 9 illustrates another embodiment of an occlusion portion 150 composed of a plurality of braided wires 152 that have a heat-set or memorized shape that causes the wires 152 to form an outer, cup shape 152A and an inner, inverted cup shape 152B. Put another way, the braided wires 152 invert to create two cylindrical layers. The braided wires 152 can be coated, laminated, covered with a film, or used with other occlusive materials as described elsewhere in this specification.

Figure 10:
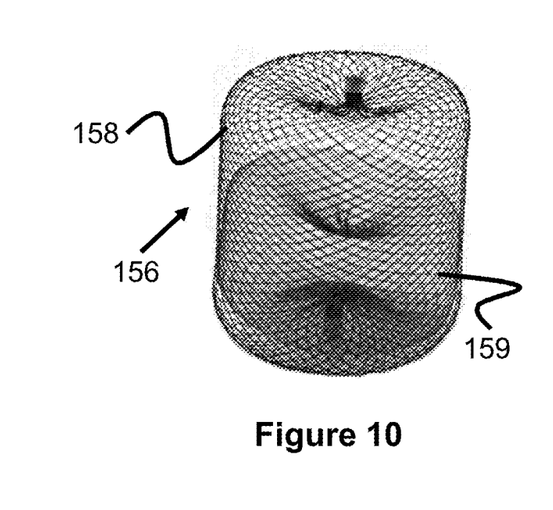
FIG. 10 is a temporary aortic occlusion device occlusion portion according to another embodiment of the present invention.

FIG. 10 illustrates yet another embodiment of an occlusion portion 156 having a generally cylindrical outer mesh layer 158 that surrounds an inner, cylindrical mesh layer 159. In one example, the outer mesh layer 158 is composed of relatively larger wires, while the inner layer 159 is composed of relatively smaller wires, which allows the inner layer 159 to have a lower porosity than the outer layer 158, since a greater amount of wires can be used (e.g., a higher pic-per-inch)—this would augment the occlusive effect of the occlusion portion by enhancing the resistance to blood flow once the blood permeates the outer layer. The outer and inner mesh layers 158, 159 can be each formed from a braided, mesh, tubular structure, or can alternately be formed from a single braided, tubular structure that is inverted to form the inner tubular layer 159. Either the outer layer 158, the inner layer 159, or both layers can be coated, laminated, covered with a film, or used with other occlusive material as described elsewhere in this specification.

Figure 11:
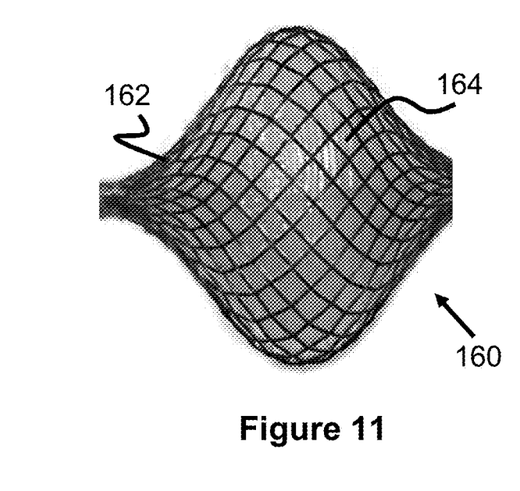
FIG. 11 is a temporary aortic occlusion device occlusion portion according to another embodiment of the present invention.

FIG. 11 illustrates another embodiment of an occlusion portion 160 having a plurality of braided wires forming a mesh layer 162, and an inner layer 164 composed of sealing, hydrophobic material such as polyurethane or silicone layer that is disposed within the mesh layer 162. Optionally, the inner layer 164 can be adhered or physically fastened to the outer mesh layer 162. Optionally, the outer surface of the mesh layer 162 can be coated, laminated, covered with a film, or used with other occlusive material as described elsewhere in this specification.

Figure 12:
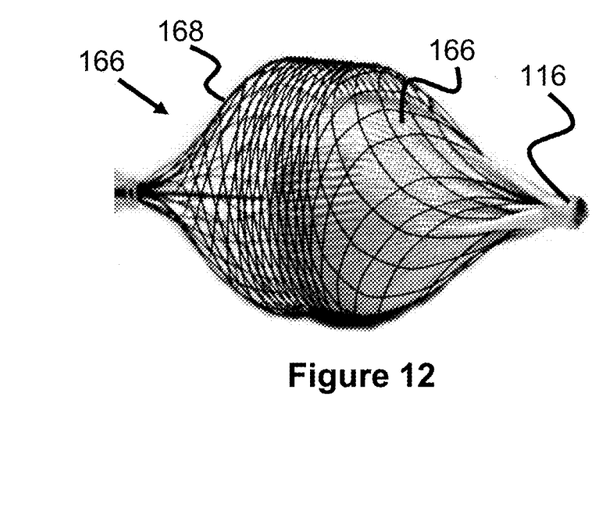
FIG. 12 is a temporary aortic occlusion device occlusion portion according to another embodiment of the present invention.

FIG. 12 illustrates another embodiment of an occlusion portion 166 having a plurality of braided wires forming a mesh layer 168, and an inner fabric material 166 fixed at a distal end of the occlusion portion 166. The inner fabric material 166 can be attached to locations around the circumference of the mesh layer 168, or can contain a wire support structure (similar to that formed by the support wires of FIG. 8) that expand the fabric material 166 when the occlusion portion 166 is expanded. The fabric material 166 can in only a proximal or distal half of the mesh layer 168, or can expand within the entire interior of the mesh layer 168. The fabric material 166 can form a funnel shape, a generally spherical shape, or similar shapes, depending on the interior shape of the mesh layer 168. The fabric material 166 can be formed from a woven fabric threads composed of a biocompatible material such as PET. Optionally, the outer surface of the mesh layer 168 can be coated, laminated, covered with a film, or used with other occlusive material as described elsewhere in this specification.

Figure 13:
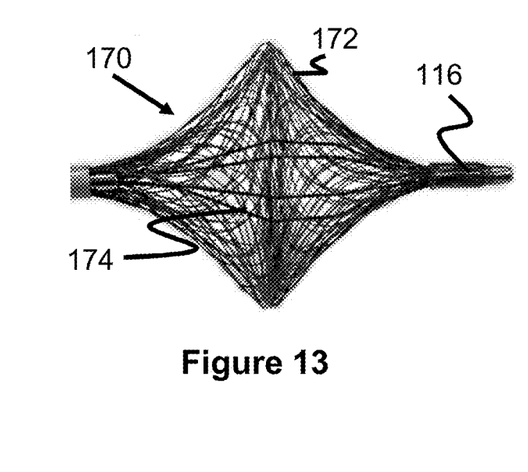
FIG. 13 is a temporary aortic occlusion device occlusion portion according to another embodiment of the present invention.

FIG. 13 illustrates another embodiment of an occlusion portion 170 which is generally similar to the embodiment of FIG. 7 in that it has a braided mesh layer 172 that has a plurality of wire struts 174 (e.g., 4) extending between its proximal and distal ends. The struts 174 are bias into a curved shape, such that they provide additional expansion force to the mesh layer 172. The mesh layer 174 forms a generally diamond shape or a shape of two cones connected together. Optionally, the outer surface of the mesh layer 168 can be coated, laminated, covered with a film, or used with other occlusive material as described elsewhere in this specification.

Figure 14:
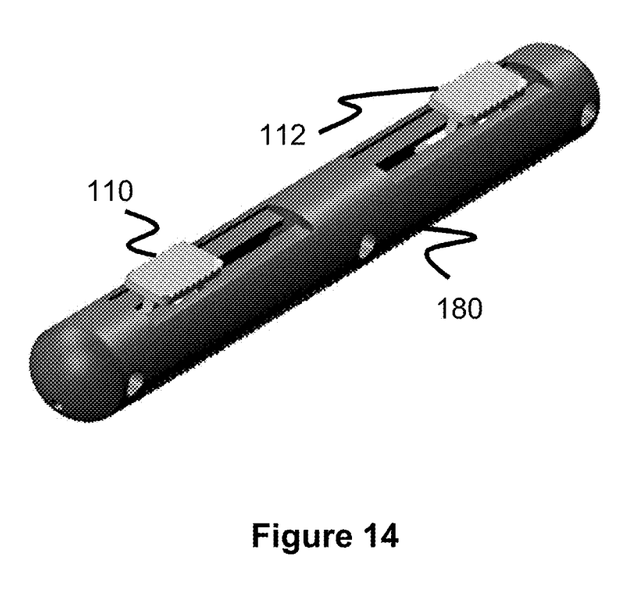
FIG. 14 is a temporary aortic occlusion device handle according to one embodiment of the present invention.
Figure 15:
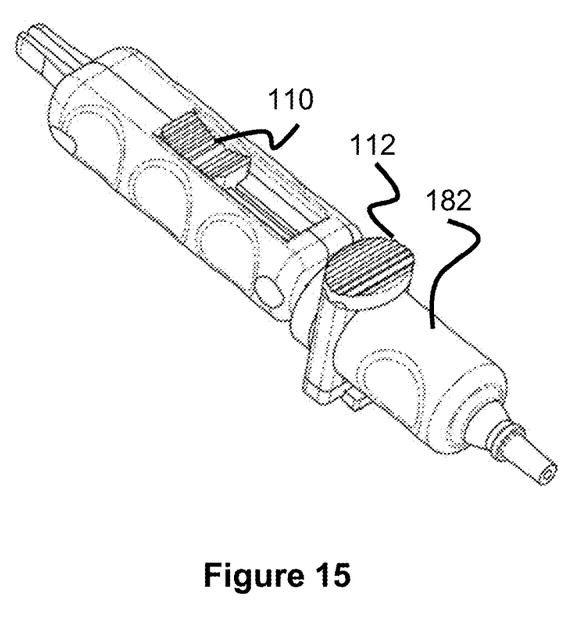
FIG. 15 is a temporary aortic occlusion device handle according to another embodiment of the present invention.

Turning to FIGS. 14 and 15, two different embodiments of handles (180, 182) are illustrated. These embodiments arrange the sliders 110, 112 in line with each other, instead of side-by-side, as in prior embodiments. Additionally, the handle 182 includes a slider 112 that is disposed entirely around the distal portion of the handle 182 and slides in a coaxial manner proximally and distally on the handle 182, the tracks are not shown but in such an embodiment slider 112 would have tracks that it slides on similar to the track that slider 110 slides on. In another embodiment, slider 112 could rotate in order to translate a connected wire—in this embodiment slider 112 would mate over the control wire in a ratcheting-type engagement where rotating slider 112 would translate the control wire which is connected to slider 112.

Figure 16:
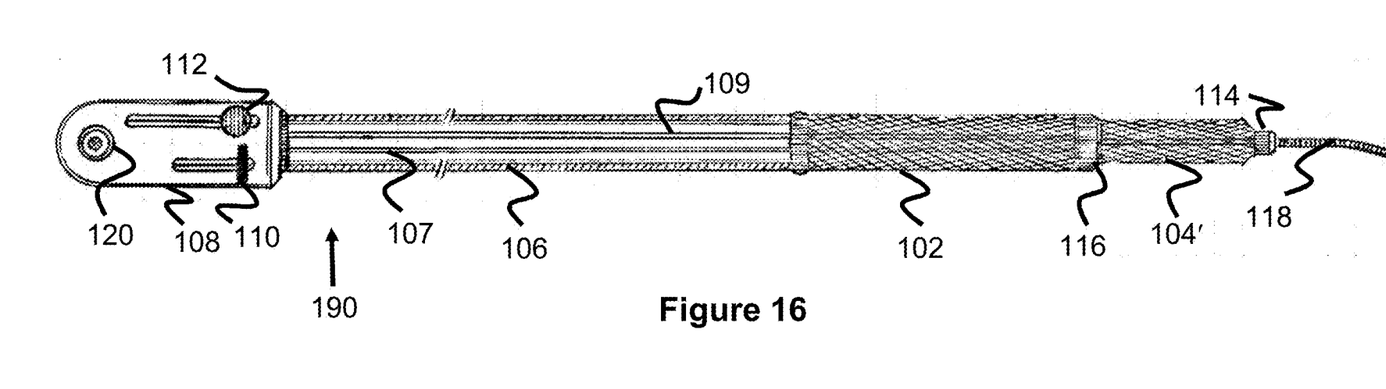
FIG. 16 is a temporary aortic occlusion device according to one embodiment of the present invention utilizing a distal locator portion and a proximal occlusion portion.
Figure 17:
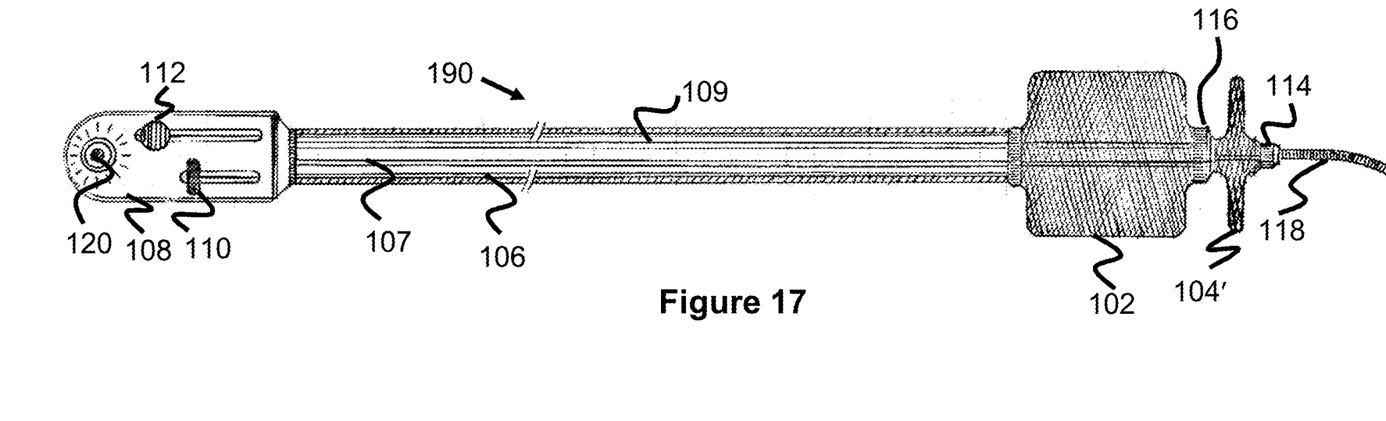
FIG. 17 is the temporary aortic occlusion device according to FIG. 16 where both the occlusion portion and the locator portion are in radially expanded configurations.

FIGS. 16 and 17 illustrate another embodiment of a temporary occlusion device 190 that is generally similar to the device 100 shown in FIGS. 1-5. However, the locator 104' is positioned distal of the occlusion portion 102.

Figure 18:
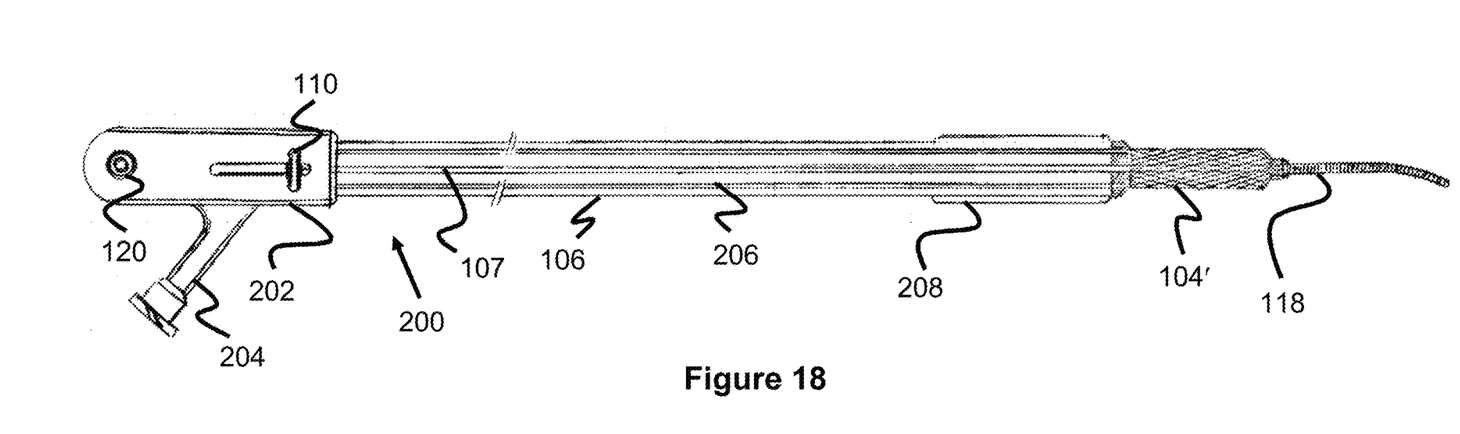
FIG. 18 is a temporary aortic occlusion device according to one embodiment of the present invention utilizing a proximal balloon and a distal locator portion.
Figure 19:
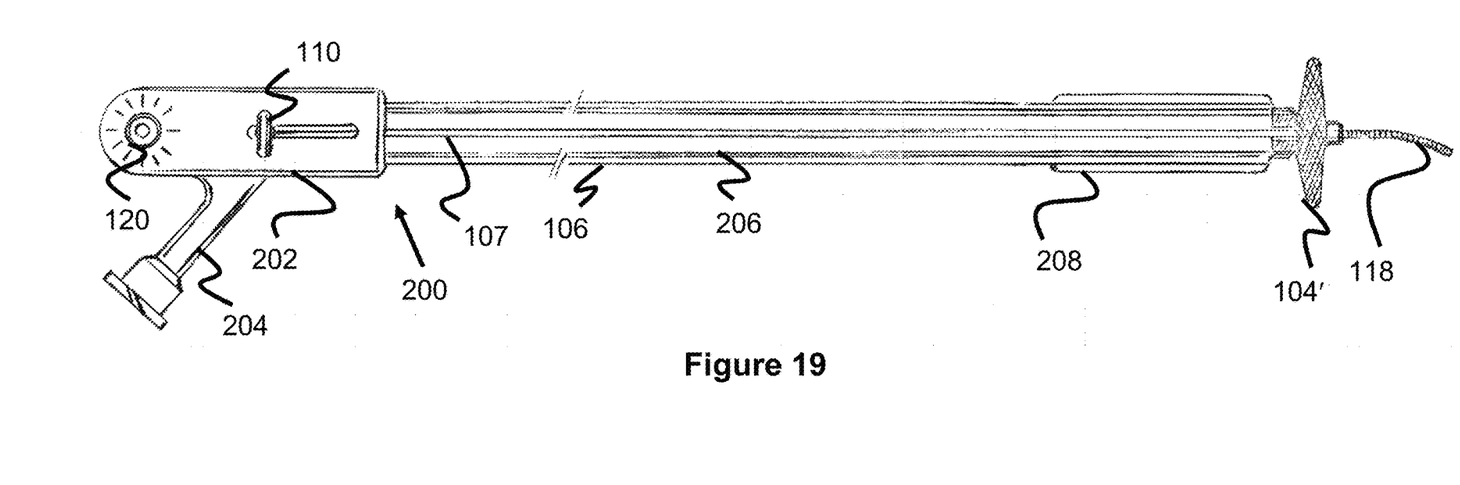
FIG. 19 is the temporary aortic occlusion device according to FIG. 18 where the locator portion is in a radially expanded configuration.
Figure 20:
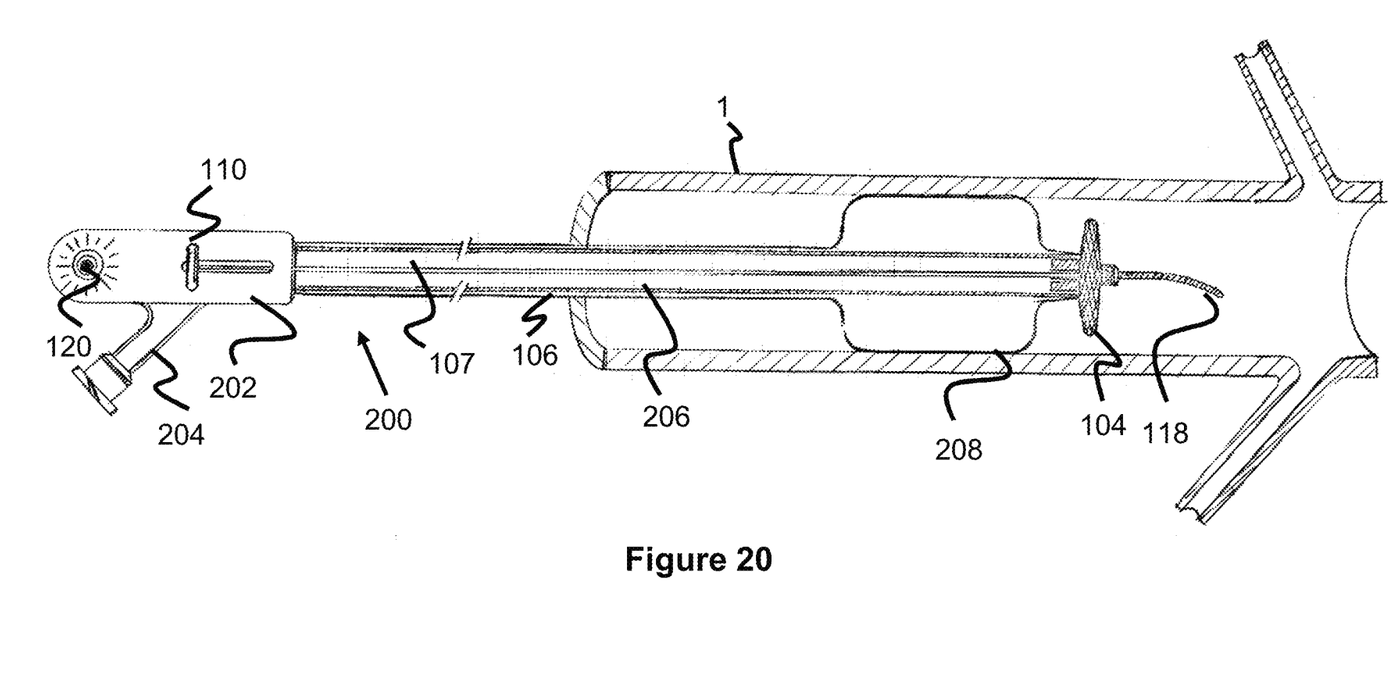
FIG. 20 is the temporary aortic occlusion device according to FIG. 18 in a blood vessel, where both the balloon and locator portions are in radially expanded configurations.

FIGS. 18-20 illustrate yet another embodiment of a temporary occlusion device 200 that is generally similar to the device 190 of FIGS. 16 and 17, including the distal location of the locator 104'. However, instead of a mesh-based occluding portion, a balloon 208 is fixed proximal of the locator 104' (alternately, the balloon 208 could be fixed distally of the locator 104). A fluid connection port is connected for a fluid source (e.g., a syringe of fluid) and is open to an interior passage 206 within the catheter tube 106, which ultimately connects to an interior of the balloon 208 to allow for selective inflation.

Preferably, the balloon 208 is composed of a highly compliant material. In this respect, if the balloon 208 is over inflated, it will elongate rather than continuing to apply radial force on the wall of the aorta, thereby avoiding balloon-induced aortic damage.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A temporary aortic occlusion device, comprising:
    an elongated device body defining an axis therethrough and having a distal end and a proximal end;
    a locator portion located near the distal end of the elongated device body, the locator portion having a proximal side and a distal side and being radially expandable from the proximal end of the device so as to confirm a proper location of the temporary aortic occlusion device within an aorta, wherein the locator portion has a maximum expansion diameter configured to be less than the diameter of the aorta;

an occlusion portion located near the distal end of the elongated device body, the occlusion portion being radially expandable from the proximal end of the device to a diameter equal to or greater than a diameter of the aorta so as to cause occlusion of the aorta; and a control member extending from the proximal end of the elongated device body to the locator portion, the control member configured to apply a compressive axial force to the locator portion to cause a relative distance between the proximal and distal sides of the locator portion to decrease thereby radially expanding the locator portion.

2. The temporary aortic occlusion device of claim 1, wherein the locator portion is composed of a plurality of braided wires.

3. The temporary aortic occlusion device of claim 1, wherein the occlusion portion is composed of a plurality of braided wires.

4. The temporary aortic occlusion device of claim 1, wherein the occlusion portion is a balloon.

5. The temporary aortic occlusion device of claim 1, wherein the locator portion is positioned proximal of the occlusion portion.

6. The temporary aortic occlusion device of claim 1, wherein the occlusion portion has a maximum expansion diameter configured to be greater than the diameter of the aorta.

7. The temporary aortic occlusion device of claim 1, wherein the maximum expansion diameter of the locator portion is smaller than a maximum expansion diameter of the occlusion portion.

8. The temporary aortic occlusion device of claim 1, wherein the elongated device body is a tube.

9. The temporary aortic occlusion device of claim 8, wherein the control member comprises a control wire positioned within a lumen of the tube controlling radial expansion of the locator portion.

10. The temporary aortic occlusion device of claim 1, further comprising a handle at the proximal end of the device.

11. The temporary aortic occlusion device of claim 10, wherein the handle includes a first slider member controlling radial expansion of the locator portion via the control member.

12. The temporary aortic occlusion device of claim 11, wherein the handle includes a second slider member controlling radial expansion of the occlusion portion.

13. The temporary aortic occlusion device of claim 11, wherein the occlusion portion is a balloon, and the handle further comprises a fluid connection port controlling radial expansion of the balloon.

14. The temporary aortic occlusion device of claim 1, wherein the temporary aortic occlusion device is configured to be located below renal arteries in an aorta.

15. The temporary aortic occlusion device of claim 1, wherein the control member is configured to apply the compressive axial force to the distal side of the locator portion.

16. A temporary aortic occlusion device, comprising:
an elongated device body having a distal end and a proximal end;
a locator portion located near the distal end of the elongated device body, the locator portion extending axially from a proximal side to a distal side in a delivery configuration and being radially expandable from the proximal end of the device so as to confirm a proper location of the temporary aortic occlusion device within the aorta by resistance, wherein the locator portion has a maximum expansion diameter configured to be less than the diameter of the aorta;
an occlusion portion located near the distal end of the elongated device body, the occlusion portion being radially expandable from the proximal end of the device so as to cause occlusion of the aorta; and
a handle at the proximal end of the elongated device body, the handle having a first expansion control member configured to control radial expansion of the locator portion by causing a compressive axial force to be applied to the locator portion and a second expansion control member configured to control radial expansion of the occlusion portion.

17. The temporary aortic occlusion device of claim 16, wherein the occlusion portion has a larger maximum expansion diameter than the maximum expansion diameter of the locator portion.

18. The temporary aortic occlusion device of claim 17, wherein the locator portion is positioned proximally of the occlusion portion.

19. The temporary aortic occlusion device of claim 16, wherein the first expansion control member is configured to apply the compressive axial force to the distal side of the locator portion.

* * * * *